(12) United States Patent
Tamura et al.

(10) Patent No.: US 7,297,311 B2
(45) Date of Patent: Nov. 20, 2007

(54) AUTOMATIC SMEAR PREPARING APPARATUS AND AUTOMATIC SAMPLE ANALYSIS SYSTEM HAVING THE SAME

(75) Inventors: Yoshiyuki Tamura, Kobe (JP); Masanori Nakaya, Kobe (JP)

(73) Assignee: Sysmex Corporation, Kobe-Shi (JP)

( * ) Notice: Subject to any disclaimer, the term of this patent is extended or adjusted under 35 U.S.C. 154(b) by 615 days.

(21) Appl. No.: 10/177,125

(22) Filed: Jun. 24, 2002

(65) Prior Publication Data

US 2003/0003022 A1 Jan. 2, 2003

(30) Foreign Application Priority Data

Jun. 29, 2001 (JP) ............................. 2001-197706

(51) Int. Cl.
*G01N 1/28* (2006.01)

(52) U.S. Cl. .................. 422/63; 422/65; 422/68.1; 422/100; 436/46

(58) Field of Classification Search ................ 422/100, 422/63, 68.1, 67, 64–66; 436/174, 46
See application file for complete search history.

(56) References Cited

U.S. PATENT DOCUMENTS

| | | | |
|---|---|---|---|
| 3,900,339 A | | 8/1975 | Filipin et al. |
| 3,906,120 A | * | 9/1975 | Geating ........................ 427/4 |
| 4,378,333 A | * | 3/1983 | Laipply ..................... 422/100 |
| 4,959,976 A | * | 10/1990 | Matsuda et al. ............... 62/271 |
| 4,961,953 A | * | 10/1990 | Singer et al. ................ 426/656 |
| 5,153,031 A | * | 10/1992 | Burlitch ...................... 427/226 |
| 5,182,078 A | * | 1/1993 | Baldi ............................. 414/9 |
| 5,194,393 A | * | 3/1993 | Hugl et al. ................... 436/525 |
| 5,209,903 A | * | 5/1993 | Kanamori et al. ............. 422/65 |
| 5,356,595 A | * | 10/1994 | Kanamori et al. ............. 422/65 |
| 5,439,649 A | * | 8/1995 | Tseung et al. ................. 422/99 |
| 5,494,828 A | * | 2/1996 | Leopando ................... 436/180 |
| 5,588,555 A | | 12/1996 | Kanamori et al. |
| 5,650,332 A | * | 7/1997 | Gao et al. .................... 436/174 |
| 5,676,910 A | * | 10/1997 | Levine et al. ................. 422/65 |
| 5,766,549 A | * | 6/1998 | Gao et al. ..................... 422/65 |
| 5,779,982 A | | 7/1998 | Aota et al. |
| 5,801,062 A | * | 9/1998 | Sarstedt et al. ............. 436/180 |
| 5,804,141 A | * | 9/1998 | Chianese ..................... 422/63 |
| 5,804,145 A | * | 9/1998 | Gao et al. ..................... 422/10 |
| 5,846,491 A | * | 12/1998 | Choperena et al. ........... 422/67 |
| 5,854,075 A | * | 12/1998 | Levine et al. ................ 436/46 |
| 6,083,759 A | * | 7/2000 | Teshima ..................... 436/174 |
| 6,086,821 A | * | 7/2000 | Lee ............................. 422/20 |
| 6,110,425 A | * | 8/2000 | Gao et al. ..................... 422/66 |
| 6,258,322 B1 | * | 7/2001 | Meikle ........................ 422/63 |
| 6,268,208 B1 | * | 7/2001 | Kondo ..................... 435/286.3 |
| 6,387,326 B1 | * | 5/2002 | Edwards et al. .............. 422/63 |
| 6,436,348 B1 | * | 8/2002 | Ljungmann et al. .......... 422/63 |
| 6,492,118 B1 | * | 12/2002 | Abrams et al. ................. 435/6 |

(Continued)

FOREIGN PATENT DOCUMENTS

FR 2639263 A 5/1990

*Primary Examiner*—Brian R. Gordon
(74) *Attorney, Agent, or Firm*—Birch, Stewart, Kolasch & Birch, LLP

(57) ABSTRACT

An automatic smear preparing apparatus includes a sample smearing section for smearing a biological sample on a slide glass by using a spreader glass, a washing section for washing the used spreader glass, and an ultrasonic generating section for applying ultrasound to the washing section.

12 Claims, 13 Drawing Sheets

U.S. PATENT DOCUMENTS

| | | |
|---|---|---|
| 6,495,106 B1 * | 12/2002 | Kalra et al. ................. 422/100 |
| 6,551,557 B1 * | 4/2003 | Rose et al. ................. 422/100 |
| 6,558,623 B1 * | 5/2003 | Ganz et al. ................... 422/63 |
| 6,572,824 B1 * | 6/2003 | Ostgaard et al. .............. 422/67 |
| 6,582,962 B1 * | 6/2003 | Richards et al. .............. 436/46 |
| 6,585,936 B1 * | 7/2003 | Shah .......................... 422/63 |
| 6,605,257 B1 * | 8/2003 | Nakazawa et al. .......... 422/100 |
| 6,793,890 B2 * | 9/2004 | Morales et al. ............... 422/99 |
| 6,948,843 B2 * | 9/2005 | Laugharn et al. ........... 366/127 |
| 6,998,270 B2 * | 2/2006 | Tseung et al. ................ 436/46 |
| 2001/0043884 A1 * | 11/2001 | Essenfeld et al. ............. 422/99 |
| 2001/0046702 A1 * | 11/2001 | Schembri ................. 435/287.2 |
| 2002/0064482 A1 * | 5/2002 | Tisone et al. ................ 422/100 |
| 2002/0110494 A1 * | 8/2002 | Lemme et al. .............. 422/100 |
| 2002/0142470 A1 * | 10/2002 | Clarke et al. ................. 436/45 |
| 2002/0173048 A1 * | 11/2002 | Nakazawa et al. .......... 436/180 |
| 2003/0129756 A1 * | 7/2003 | Thorne et al. ................ 436/46 |
| 2003/0138355 A1 * | 7/2003 | Tamura et al. ................ 422/63 |
| 2003/0203493 A1 * | 10/2003 | Lemme et al. ................ 436/46 |
| 2003/0231983 A1 * | 12/2003 | Schleifer ...................... 422/50 |
| 2004/0001860 A1 * | 1/2004 | Cheung ................. 424/195.16 |
| 2004/0002163 A1 * | 1/2004 | Reinhardt et al. ........... 436/174 |
| 2004/0033169 A1 * | 2/2004 | Shah .......................... 422/100 |
| 2004/0241875 A1 * | 12/2004 | Dales et al. ................. 436/180 |
| 2005/0025672 A1 * | 2/2005 | Nakaya et al. .............. 422/100 |
| 2005/0053526 A1 * | 3/2005 | Angros ....................... 422/100 |
| 2006/0029519 A1 * | 2/2006 | Nakaya et al. ................ 422/63 |
| 2006/0051240 A1 * | 3/2006 | Watanabe .................... 422/67 |

* cited by examiner

AUTOMATIC SMEAR PREPARING APPARATUS AND AUTOMATIC SAMPLE ANALYSIS SYSTEM HAVING THE SAME

CROSS-REFERENCE TO RELATED APPLICATION

This application is related to Japanese Patent Application No. 2001-197706 filed on Jun. 29, 2001, whose priority is claimed under 35 USC §119, the disclosure of which is incorporated by reference in its entirety.

BACKGROUND OF THE INVENTION

1. Field of the Invention

The present invention relates to an automatic smear preparing apparatus for preparing a smear of a sample collected from a living body such as blood or bone marrow fluid and an automatic sample analysis system having the same.

2. Description of Related Art

U.S. Pat. No. 5,779,982 describes an automatic blood smear preparing apparatus which automatically performs all the steps of smearing of a blood sample onto a slide glass and staining of the blood sample. This apparatus utilizes a cassette capable of carrying the slide glass and a stain solution therein. That is, the sample is smeared on the slide glass, the slide glass is held in the cassette and the stain solution is injected in the cassette to stain the smeared sample.

According to the conventional automatic blood smear preparing apparatus as described above, blood is dropped onto the slide glass and smeared thereon by using a spreader glass and then the spreader glass used is washed by immersing it into washing liquid contained in a washing bath. However, if the spreader glass is not washed enough, protein or the like remains thereon and it is difficult to prepare a satisfactory smear.

SUMMARY OF THE INVENTION

In view of the above-mentioned circumstances, the present invention has been achieved to provide an automatic smear preparing apparatus and an automatic sample analysis system having the same, wherein the automatic smear preparing apparatus is provided with a washing device capable of effectively removing contaminants such as protein deposited on the spreader glass, thereby satisfactorily maintaining quality of the smear.

The present invention provides an automatic smear preparing apparatus comprising: a sample smearing section for smearing a biological sample on a slide glass by using a spreader glass; a washing section for washing the spreader glass used; and an ultrasonic generating section for applying ultrasound to the washing section.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Figure 1:
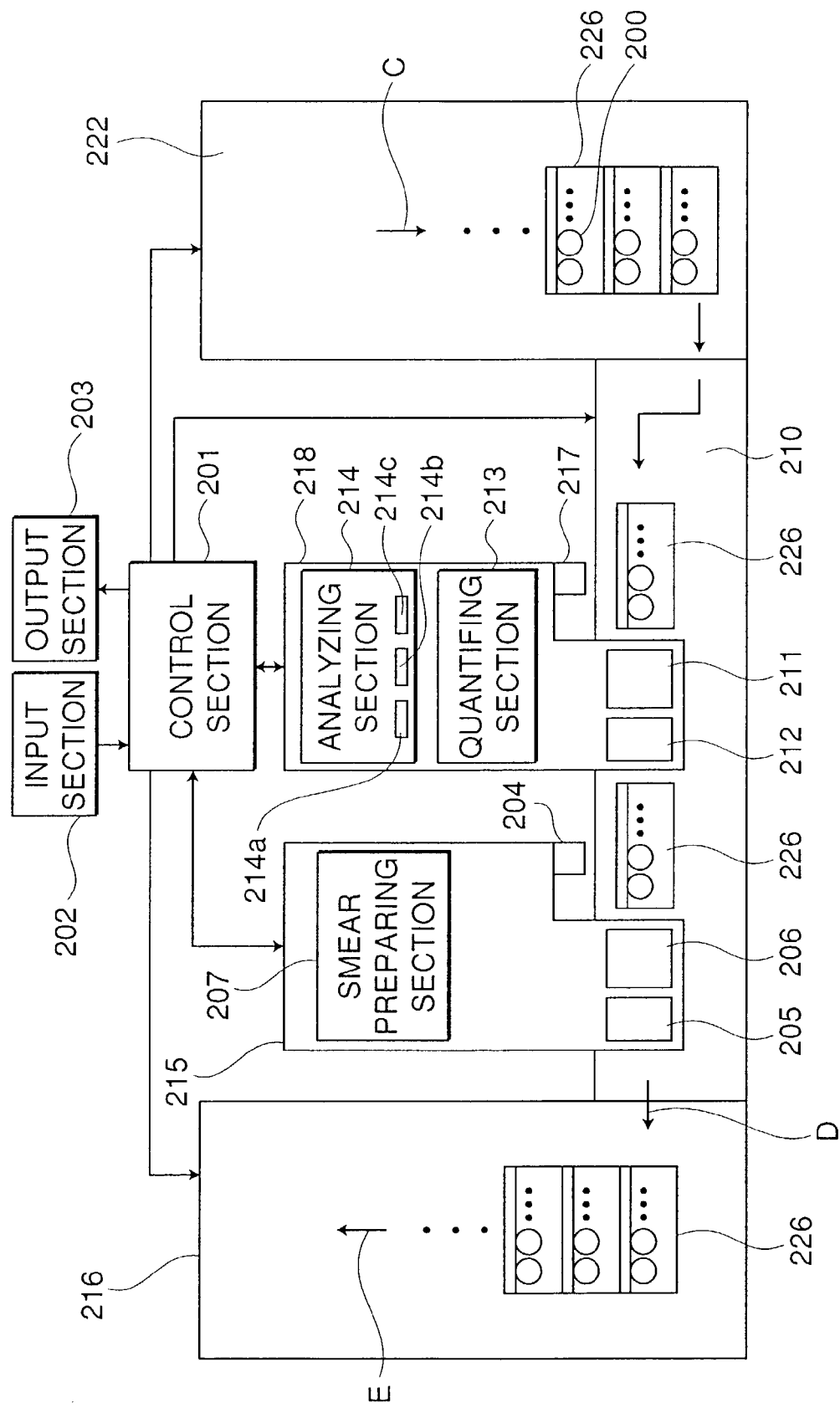
FIG. 1 is a plan view illustrating a blood analysis system according to the present invention.

An automatic smear preparing apparatus includes a sample smearing section for smearing a biological sample on a slide glass by using a spreader glass; a washing section for washing the used spreader glass; and an ultrasonic generating section for applying ultrasound to the washing section.

The biological sample referred to in the present invention includes blood and bone marrow fluid of mammals including human being.

The automatic smear preparing apparatus according to the present invention signifies such an apparatus that automatically performs all the steps of a preparation process including sucking from a sample container a biological sample such as blood contained therein, smearing the sample on a slide glass, staining the smeared sample and carrying the slide glass out.

According to the present invention, the slide glass may be a commercially available one generally used for microscopes. For example, there can be used a transparent glass plate in a rectangular shape having an area of 26 mm×76 mm and a thickness of 1 mm.

The sample smearing section is constructed such that the biological sample is dropped onto the slide glass and spread over the surface of the slide glass by using the spreader glass. For example, a quartz glass plate in a square shape having the same width and thickness as the slide glass can be used as the spreader glass.

The sample smearing section preferably has a mechanism in which the spreader glass is contacted on the slide glass at an angle of 30°±10° and slid on the slide glass under a predetermined pressure.

The washing section may include a sub-washing section for spraying washing liquid onto the spreader glass and a main washing section for immersing the spreader glass in the washing liquid.

In this case, the sub-washing section sprays the washing liquid onto the spreader glass in order to wash and sufficiently wet the spreader glass with the washing liquid. Accordingly, when the spreader glass is immersed in the washing liquid in the main washing section, wettability of the spreader glass is improved to facilitate the washing process in the main washing section. Water or physiologic saline may suitably be used as the washing liquid.

The sub-washing section preferably includes two nozzles for discharging the washing liquid onto both surfaces of the spreader glass, respectively, and a shifting section for shifting the two nozzles in parallel with the spreader glass. Thereby, both surfaces of the spreader glass can be washed at the same time and wetted uniformly.

The main washing section preferably includes a washing bath for containing the washing liquid and a transferring section for putting the spreader glass in and out of the washing bath.

The transferring section preferably puts the spreader glass in and out of the washing bath in a direction vertical to the washing liquid, which prevents contaminants from redepositing on the spreader glass.

The washing liquid discharged from the nozzles may be received in the washing bath.

The ultrasonic generating section is capable of applying ultrasound to any of the spreader glass, the sub-washing section and the main washing section.

The ultrasonic generating section includes an ultrasonic transducer, which may be arranged in the washing bath. The ultrasonic transducer may suitably be placed on the outer surface of the bottom or the side wall of the washing bath. Alternatively, the ultrasonic transducer may be disposed inside the washing bath.

The ultrasonic transducer may be a commercially available one. The transducer generally has a structure in which a piezoelectric element is sandwiched between two electrode plates and an alternating voltage is applied between the electrodes to excite the piezoelectric element in a direction orthogonal to the polarization direction.

The ultrasonic generating section may further include a driving section for driving the ultrasonic transducer.

The driving section includes, for example, an a.c. inverter for applying a driving a.c. voltage to the ultrasonic transducer. The ultrasonic transducer utilizing the piezoelectric element is characterized in that the greater the amplitude of the applied a.c. voltage is, the greater the amplitude of the ultrasound becomes. As a result, the generated ultrasound becomes greater. Therefore, if the driving section is provided with the a.c. inverter capable of changing the output voltage, thereby the ultrasound can be adjusted. The ultrasonic transducer preferably has the frequency range of 50 to 80 kHz.

The driving section preferably drives the ultrasonic transducer in such a manner that the greater viscosity the biological sample has, the greater the ultrasound that is generated.

Thus, the biological sample adhered to the spreader glass can effectively be washed away in accordance with the viscosity (tackiness) thereof. In the case where the biological sample is blood, the viscosity thereof is determined by the number of erythrocytes, the number of leukocytes, the amount of hemoglobin, the hematocrit value or the like.

In this case, the viscosity of the biological sample is preferably obtained by an analyzer which analyzes the biological sample by at least one of an optical analysis method or an electrical analysis method.

The driving section may adjust the ultrasound by intermittently driving the ultrasonic transducer in a predetermined period.

The driving section preferably drives the ultrasonic transducer when the spreader glass is put in the washing bath and stops the transducer when the spreader glass is taken out of the washing bath. This prevents the washing liquid from spilling out of the washing bath due to the ultrasonic energy of the transducer.

Further, the present invention provides an automatic smear preparing apparatus comprising: a sample smearing section for smearing a biological sample on a slide glass by using a spreader glass; a washing section for washing the used spreader glass; and an ultrasonic generating section for applying ultrasound to the washing section, wherein the ultrasonic generating section includes an ultrasonic transducer and a driving section for driving the ultrasonic transducer, the driving section driving the ultrasonic transducer so that the greater the viscosity of the biological sample, the greater the ultrasound that is generated.

Still further, the present invention provides an automatic sample analysis system comprising an automatic sample analyzer for analyzing components of a biological sample and an automatic smear preparing apparatus. It is preferred that the automatic smear preparing apparatus prepares a smear of a biological sample analyzed by the automatic sample analyzer and that the viscosity of the biological sample is calculated by analysis results of the biological sample.

The automatic sample analyzer may include a quantifying section for quantifying the sample and an analyzing section for analyzing the quantified sample by at least one of an optical analysis method and an electrical analysis method.

The optical analysis method may use at least one of flow cytometry and absorbance determination, and the electrical analysis method may use a method of measuring electric resistance of the sample passing through an orifice.

Hereinafter, the present invention is detailed by way of embodiments with reference to the figures. However, the present invention is not limited thereto.

Automatic Sample Analysis System

FIG. 1 is a plan view illustrating a structure of a blood analysis system which is an example of an automatic sample analysis system according to the present invention.

As shown in FIG. 1, a blood analyzer 218 and a smear preparing apparatus 215 are arranged in the center of the blood analysis system. On the right side of the system, provided is a rack sending section 222 which stores a plurality of racks 226 each carrying sample containers 200 and sends the racks one by one. On the left side, a rack collecting section 216 for collecting and storing the racks 226 is provided. Between the rack sending section 222 and the rack collecting section 216, provided is a transferring section 210 for transferring (transversely carrying) the racks 226 one by one from the rack sending section 222 to the rack collecting section 216.

The blood analyzer 218 includes a barcode reader 217 for reading a barcode on each sample container 200, sample stirrer 211 for stirring a sample in the sample container 200, a suction apparatus 212 for sucking the stirred sample from the sample container 200, a quantifying section 213 for quantifying the sucked sample and an analyzing section 214 for analyzing the quantified sample.

The analyzing section 214 includes an optical analysis section 214a for optically analyzing components of the sample by flow cytometry, an electrical analysis section 214b for analyzing the components of the sample by measuring electric resistance of the sample passing through an orifice and an absorbance analysis section 214c for analyzing the components of the sample by an absorbance of the sample.

A smear preparing apparatus 215 includes a barcode reader 204 for reading the barcode on the sample container 200, a sample stirrer 206 for stirring the sample in the sample container 200, a suction apparatus 205 for sucking the stirred sample from the sample container 200 and a smear preparing section 207 for preparing a smear of the sucked sample.

In the neighborhood of the blood analyzer 218, a control section 201, an input section 202 for inputting analysis conditions and an output section 203 are provided. The control section 201 includes a personal computer in this case to control the rack sending section 222, the transferring section 210, the rack collecting section 216, the blood analyzer 218 and the smear preparing apparatus 215 in accordance with output signals from the input section 202 (a keyboard in this case) and the barcode readers 204 and 217.

The control section 201 receives analysis data from the analyzing section 214 and analyzes the numbers and the particle sizes of erythrocytes, leukocytes and platelets contained in the sample, the hemoglobin concentration and the hematocrit value. Further, the control section 201 calculates the viscosity of the sample from the analysis results. The output section 203 herein is made of a CRT and a printer and outputs the input analysis conditions and the results of the analysis.

Figure 2:
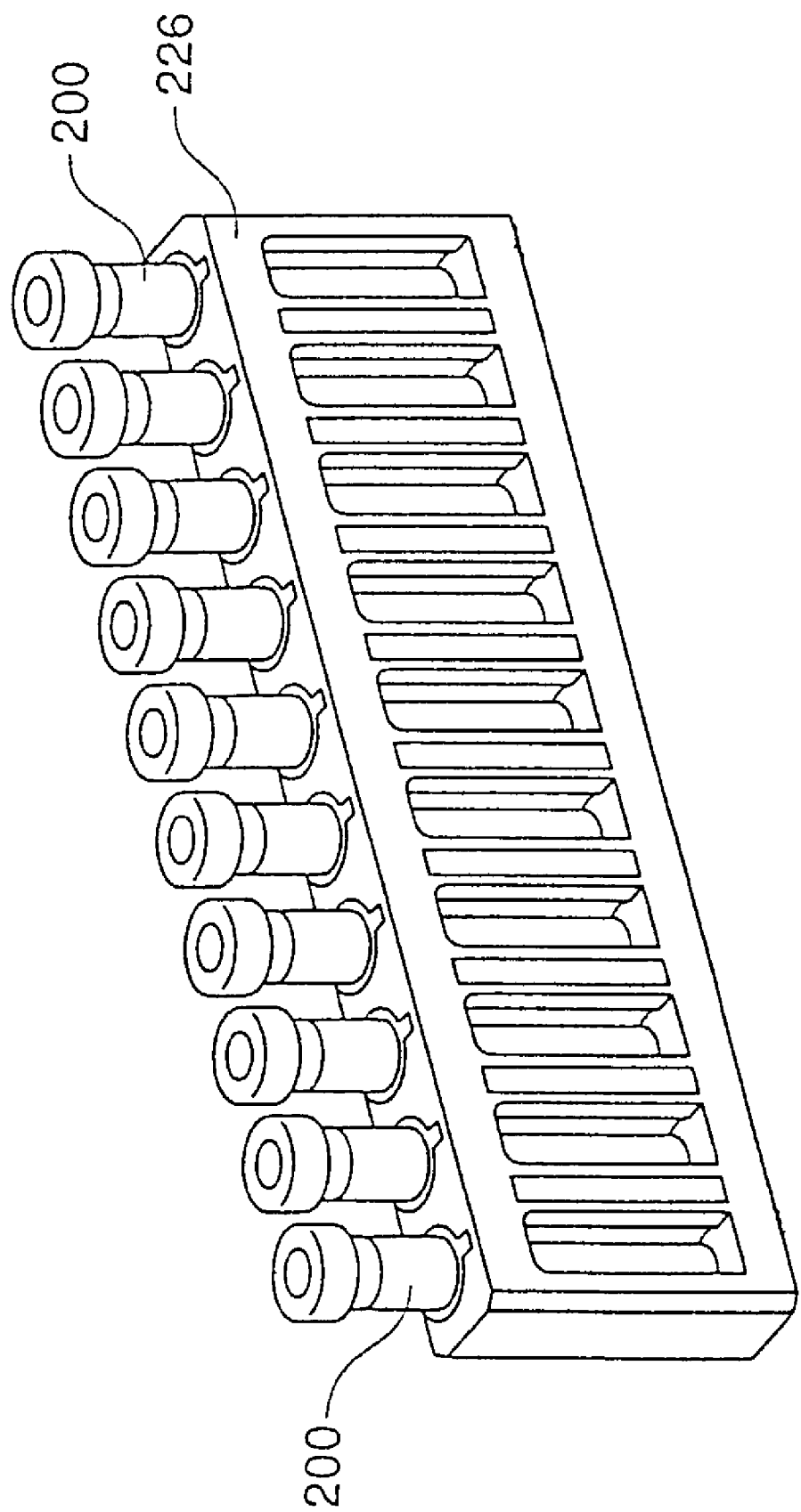
FIG. 2 is a perspective view illustrating a rack used in the blood analysis system according to the present invention.

Each rack 226 is configured in the form of a tube rack as shown in FIG. 2 and ten sample containers 200 can be mounted thereon. The sample container 200 is in the form of a cylinder having a bottom, i.e., in the form of a test tube. A top opening thereof is sealed with a cap and blood is contained inside as the sample.

As shown in FIG. 1, when the racks 226 carrying the sample containers 200 are arranged in a vertical line in the rack sending section 222, all the racks 226 serially travel in the direction indicated by an arrow C. Then, the rack 226 at the forefront is sent to the transferring section 210 on the left hand to be transferred in the transverse direction.

Above the transferring section 210, part of the blood analyzer 218 is arranged. The rack 226 transferred by the transferring section 210 is stopped in a position where the sample container 200 at the forefront is opposed to the barcode reader 217. After the barcode reader 217 reads the barcode on the sample container 200, the sample container 200 is transferred again in the transverse direction and stopped at a position immediately below the stirrer 211 of the blood analyzer 218.

After the sample is stirred by the sample stirrer 211, the rack 226 travels only a predetermined distance (a pitch distance between the sample containers 200). Then, the suction apparatus 212 sucks the stirred sample out of the sample container 200.

The sucked sample is quantified in the quantifying section 213 and analyzed in the analyzing section 214. During the suction process by the suction apparatus 212, the stirrer 211 stirs the sample in the following sample container 200.

The racks 226 are intermittently transferred by the pitch distance between the sample containers 200 and the barcode reader 204 of the smear preparing apparatus 215 sequentially reads the barcodes on the sample containers 200 that have gone through the analysis. The control section 201 identifies from the barcodes the sample which should be prepared as a smear according to the analysis results, and the corresponding sample is stirred by the stirrer 206. Then, the stirred sample is sucked from the sample container 200 by the suction apparatus 205 to prepare the smear in the smear preparing section 207.

After the ten sample containers (all sample containers carried on a single rack 226) are subjected to the suction process for sucking the sample which needs to be prepared as a smear, the rack 226 is transferred in the direction of an arrow D to be collected in the rack collecting section 216 in the direction of an arrow E. The racks 226 are sequentially sent from the rack sending section 222 to the transferring section 210 at a predetermined distance and the above-mentioned treatment is performed repetitively with respect to the sample containers 200 on each rack 226.

Smear Preparing Apparatus

Figure 3:
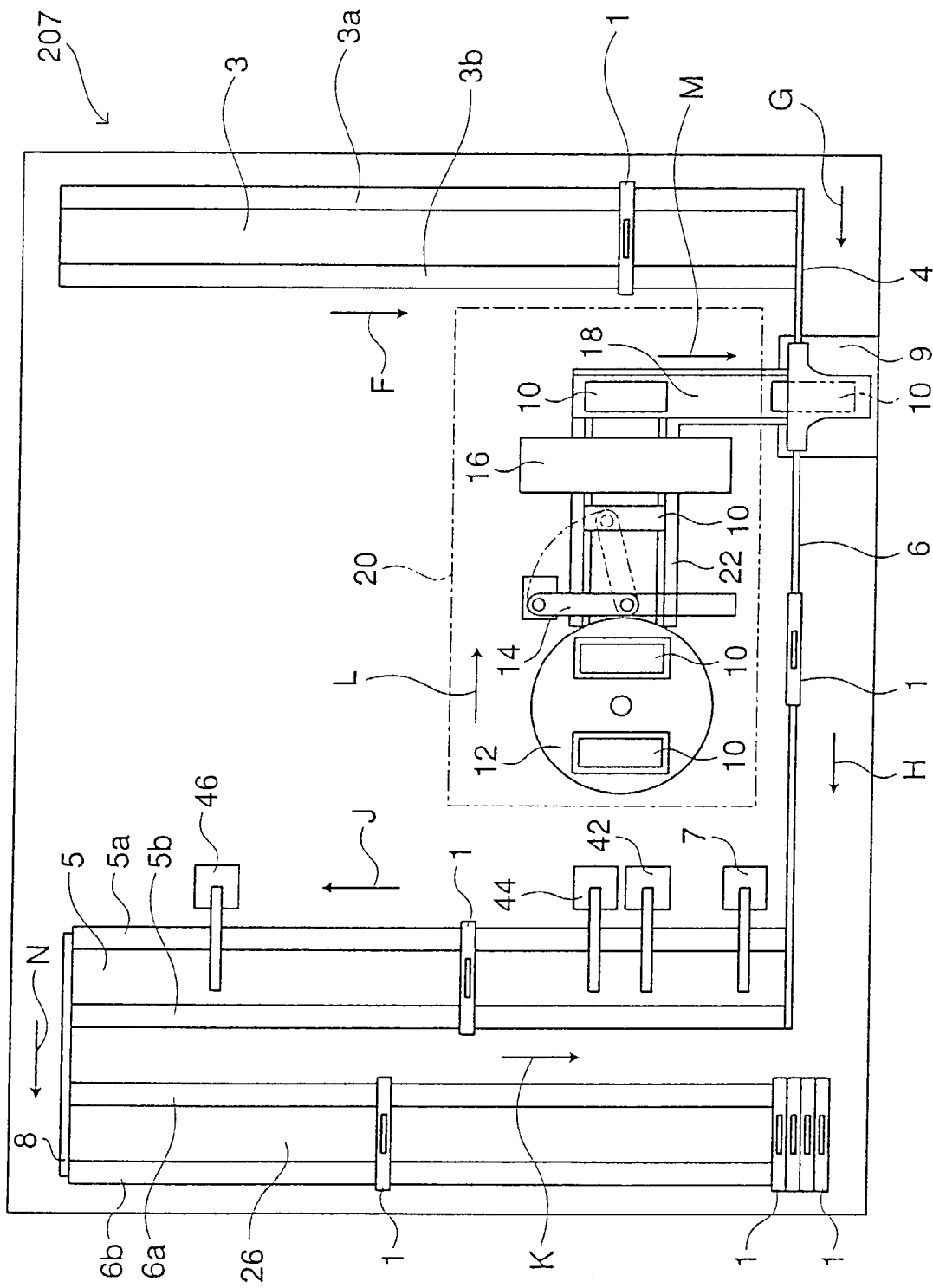
FIG. 3 is a plan view illustrating a smear preparing section according to the present invention.
Figure 4:
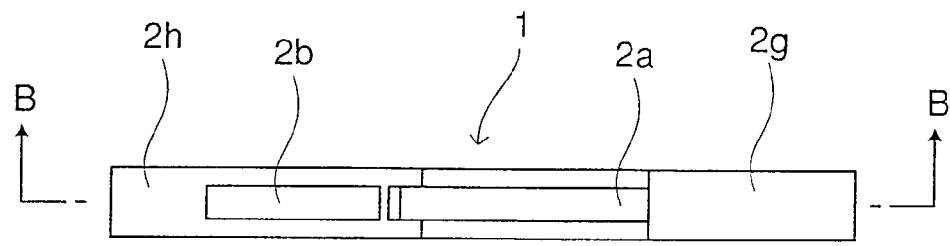
FIG. 4 is a top view illustrating a cassette used in the smear preparing section according to the present invention.
Figure 5:
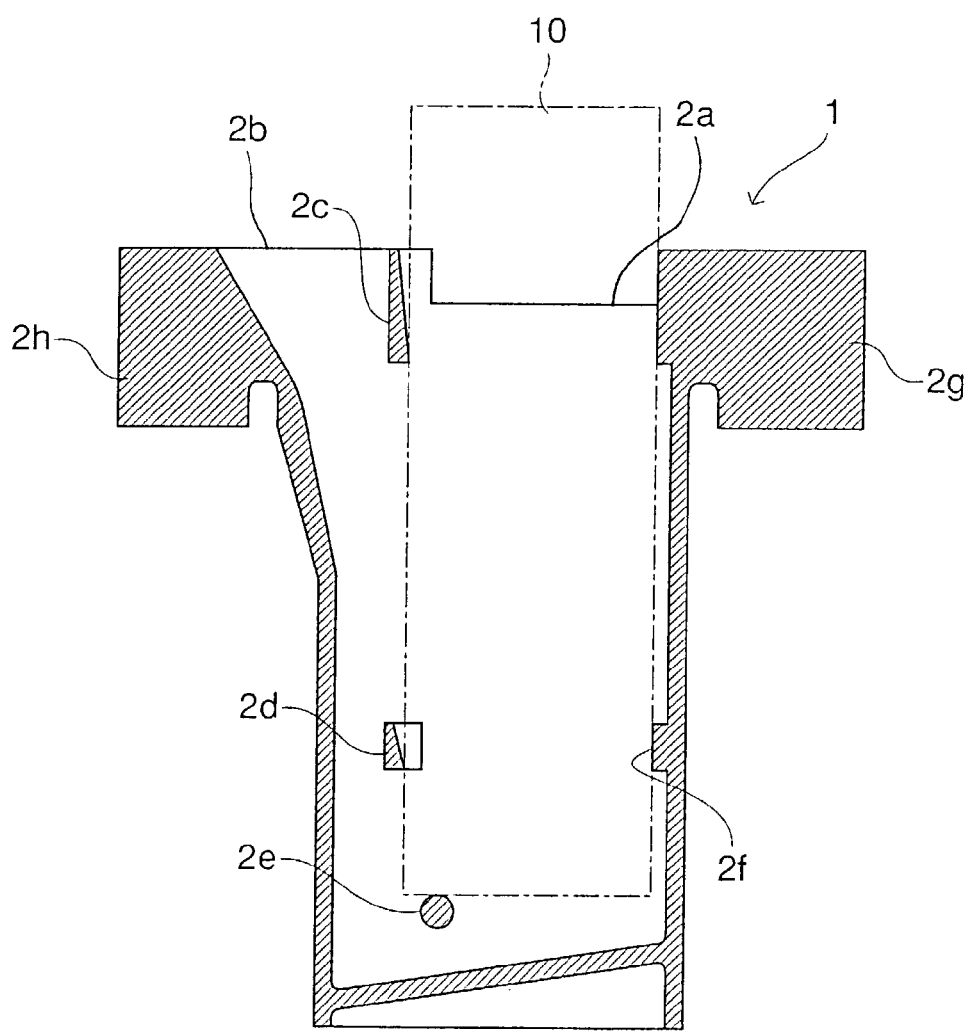
FIG. 5 is a fragmentary view taken in the direction of arrows along a line B-B of FIG. 4.

FIG. 3 is a plan view illustrating a smear preparing section 207 of the smear preparing apparatus 215, FIG. 4 is a top view of a cassette for holding a slide glass on which a sample has been smeared and FIG. 5 is a fragmentary view taken in the direction of arrows along a line B-B of FIG. 4.

As shown in FIG. 4, a cassette 1 is formed of a hollow thin plate. On the top surface thereof, provided are an insert hole 2a through which a slide glass is inserted into the cassette 1 and an injection hole 2b through which a stain solution and drying air are injected into the cassette 1. Referring to FIG. 5, supporting parts 2c to 2f are provided inside the cassette 1 to support a slide glass 10 inserted through the insert hole 2a.

Since an adequate clearance is ensured between both surfaces of the slide glass 10 and inner surfaces of the cassette 1, the stain solution and the air in the cassette 1 can easily contact the both surfaces of the slide glass 10. The cassette 1 has hooks 2g and 2h extending in a horizontal direction from both shoulders, so that the cassette 1 is hung on transfer belts by the hooks 2g and 2h as mentioned later.

As shown in FIG. 3, the smear preparing section 207 includes a smearing section 20 for smearing the sample on the slide glass 10, a conveyer 3 for conveying an empty cassette 1 in the direction of an arrow F by hanging it on belts 3a and 3b, a receiving operation section 9 for receiving the smeared slide glass 10 in the empty cassette 1 and a conveyer 4 for conveying the empty cassette 1 from the conveyer 3 to the receiving operation section 9 in the direction of an arrow G.

Further, the smear preparing section 207 includes a conveyer 6 which conveys the cassette 1 carrying the slide glass 10 from the receiving operation section 9 toward the direction of an arrow H, a conveyer 5 which receives the cassette 1 from the conveyer 6 to send it toward the direction of an arrow J by hanging it on belts 5a and 5b, a conveyer 8 which receives the cassette 1 from the conveyer 5 to transfer it in the direction of an arrow N and a storage conveyer 26 which receives the cassette 1 from the conveyer 8 to transfer it in the direction of an arrow K by hanging it on belts 6a and 6b and stores the cassette 1.

In the smearing section 20, a plurality of slide glasses 10 are placed on a turntable 12 and are taken one by one to be transferred in the direction of an arrow L by a conveyer 22. A sample sucked by the suction apparatus 205 (see FIG. 1) is dropped onto the slide glass 10 by a dispensing mechanism 14 and smeared by a smearing mechanism 16. The slide glass 10 on which the sample is smeared is mounted on a conveyer 18 to be transferred in the direction of an arrow M, and then received in the empty cassette 1 in the receiving operation section 9.

At the forefront of the conveyer 5, a first treatment section 7 for treating the smeared slide glass 10 is provided. The first treatment section 7 injects a May-Grunwald solution (in which 99% is methanol) in the cassette 1 to immerse the slide glass 10 therein for a predetermined period. Then, air is blown to the smeared surface of the slide glass 10 to evaporate the liquid component thereon, thereby drying the smeared surface.

Then, the first treatment section 7 injects the May-Grunwald solution again in the cassette 1 to immerse the slide glass 10 therein.

Subsequently, the May-Grunwald solution is drained out of the cassette 1 in a second treatment section 42 and a May-Grunwald dilution is injected in the cassette 1. The slide glass 10 in the cassette 1 is immersed in the May-Grunwald dilution for a predetermined period while the cassette 1 is conveyed in the direction of the arrow J.

Then, in a third treatment section 44, the May-Grunwald dilution is drained out of the cassette 1 and a Giemsa solution is injected. The slide glass 10 in the cassette 1 is immersed in the Giemsa solution for a predetermined period while the cassette 1 is conveyed in the direction of the arrow J.

Then, in a fourth treatment section 46, the Giemsa solution is drained out of the cassette 1 and washing liquid is dispensed and drained, thereby the slide glass 10 is washed. Thus, the smeared sample on the slide glass 10 is double-stained with the May-Grunwald and Giemsa solutions.

Thereafter, air is blown in the cassette 1 to dry the stained slide glass 10.

The cassette 1 carrying the stained slide glass 10 is sent to the storage conveyer 26 via the conveyer 8 and stored therein.

Then, by an operator, the cassette is taken out of the storage conveyor 26 and the slide glass 10 is placed under a microscope for blood cell observation.

Smearing Mechanism

Figure 6:
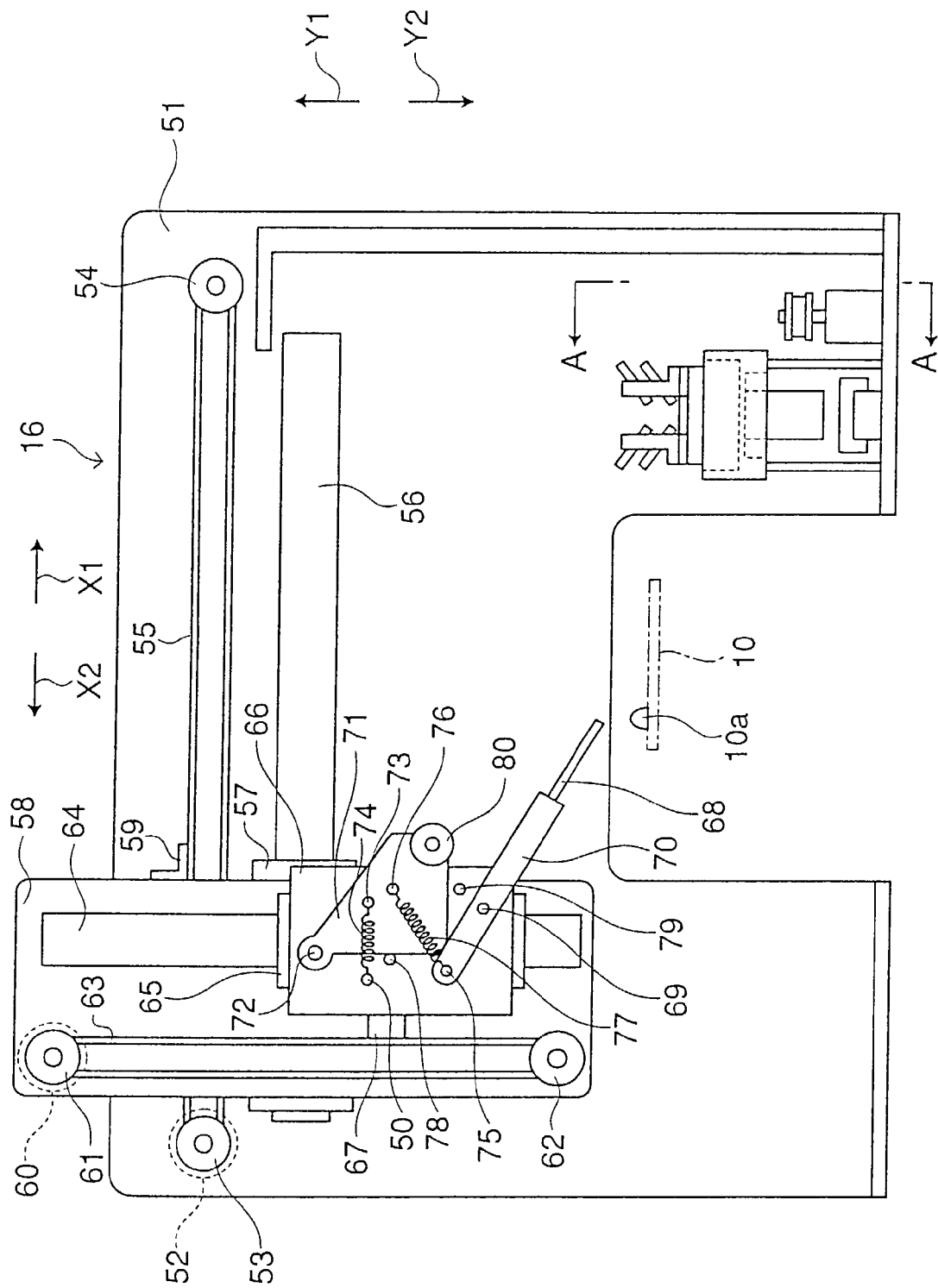
FIG. 6 is a front view illustrating a smearing mechanism according to the present invention.

FIG. 6 is a front view illustrating the smear mechanism 16. As shown in FIG. 6, the smear mechanism 16 includes a base plane 51. The base plane 51 includes a drive pulley 53 which is driven by a stepping motor 52 mounted on a rear surface of the base flame 51, a follower pulley 54 which is rotatably supported on a front surface thereof, a timing belt 55 entrained about the pulleys 53 and 54 and a rail 56 arranged in parallel with the timing belt 55.

The rail 56 supports a sliding member 57 such that the sliding member 57 can slide in the direction of arrows X1 and X2. The sliding member 57 is equipped with a horizontally moving plate 58 which is connected to the timing belt 55 via a connector 59.

The horizontally moving plate 58 includes a stepping motor 60 provided on its rear surface. On its front surface, a drive pulley 61 which is driven by the stepping motor 60, a follower pulley 62 which is rotatably supported and a timing belt 63 entrained about the pulleys 61 and 62 are provided. The horizontally moving plate 58 includes a rail 64 arranged in parallel with the timing belt 63. The rail 64 supports a sliding member 65 such that the sliding member 65 can slide in the directions of arrows Y1 and Y2.

On the sliding member 65, mounted is a vertically moving plate 66 which is connected to the timing belt 63 via a connector 67. A support arm 70 which supports a spreader glass 68 at one end is rotatably supported by a pivot pin 69 on the vertically moving plate 66. Further, a cam 71 equipped with a freely rotatable ball bearing 80 is supported rotatably by a pivot pin 72 on the vertically moving plate 66.

A pin 50 formed upright on the vertically moving plate 66 and a pin 73 formed upright on the cam 71 are connected via a tensile spring 74. A pin 75 formed upright on the other end of the support arm 70 and a pin 76 formed upright on the cam 71 are connected via a tensile spring 77. Further, two stop pins 78 and 79 are formed upright on the vertically moving plate 66.

As shown in FIG. 6, the cam 71 is biased toward a clockwise direction by the spring 74 to abut the stop pin 78, while the support arm 70 is biased toward a clockwise direction by the spring 77 to abut the cam 71. The cam 71 and the support arm 70 stand still in this state.

Figure 7:
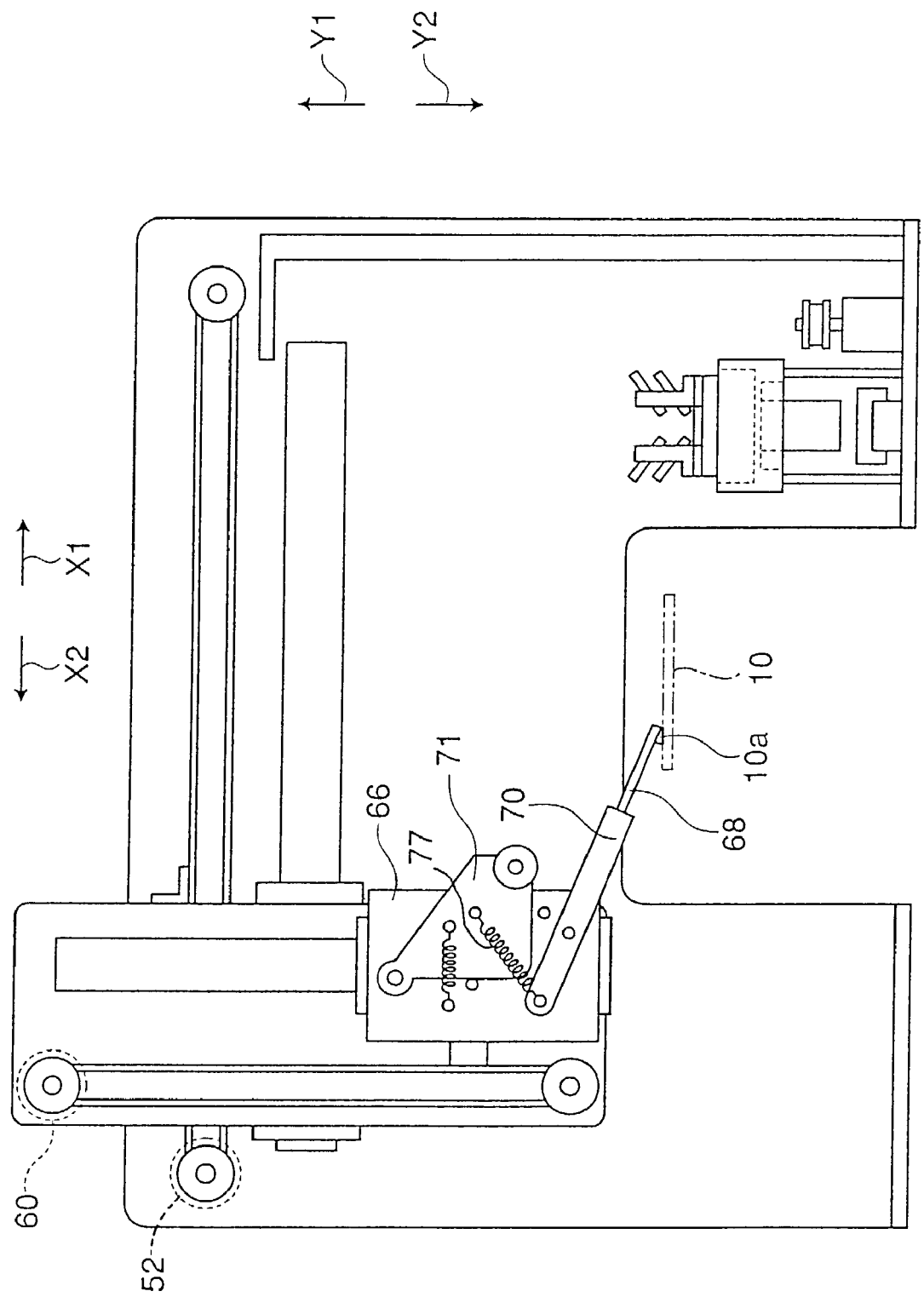
FIG. 7 is a view illustrating the operation of the smearing mechanism according to the present invention.

In the above-described structure, a sample 10a is dropped onto the slide glass 10 and the slide glass 10 is transferred to a position shown in FIG. 6 by the conveyer 22 (see FIG. 3). Then, the stepping motor 60 is driven to move the spreader glass 68 downward so that the spreader glass 68 contacts the slide glass 10 at an angle of about 30° as shown in FIG. 7. Thus, the support arm 70 comes off the cam 71 and an edge of the spreader glass 68 presses the slide glass 10 under the bias force of the spring 77.

Then, the stepping motor 52 is driven to shift the spreader glass 68 in the direction of the arrow X1, thereby the sample 10a is smeared on the surface of the slide glass 10.

Subsequently, the stepping motor 60 is driven to move the spreader glass 68 upward. The smeared slide glass 10 is received in the cassette 1 as mentioned above and subjected to the staining process.

Spreader Glass Washing Apparatus

Figure 8:
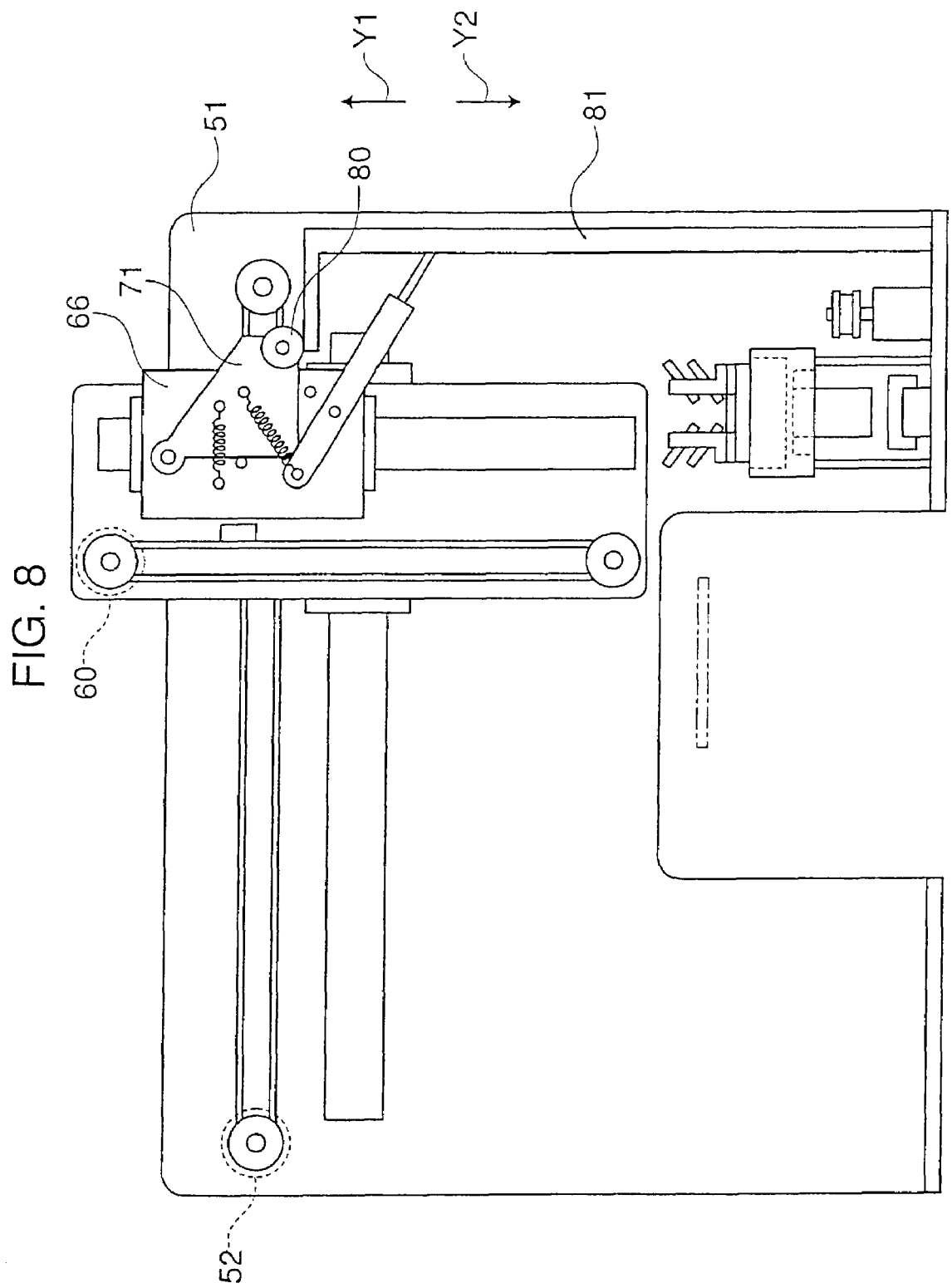
FIG. 8 is a view illustrating the operation of the smearing mechanism according to the present invention.

After the above-mentioned smearing process is finished, the stepping motors 52 and 60 are driven to shift the vertically moving plate 66 to a position shown in FIG. 8. Then, the bearing 80 of the vertically moving plate 66 is engaged with a bearing supporting bracket 81 provided upright on the base flame 51.

Figure 9:
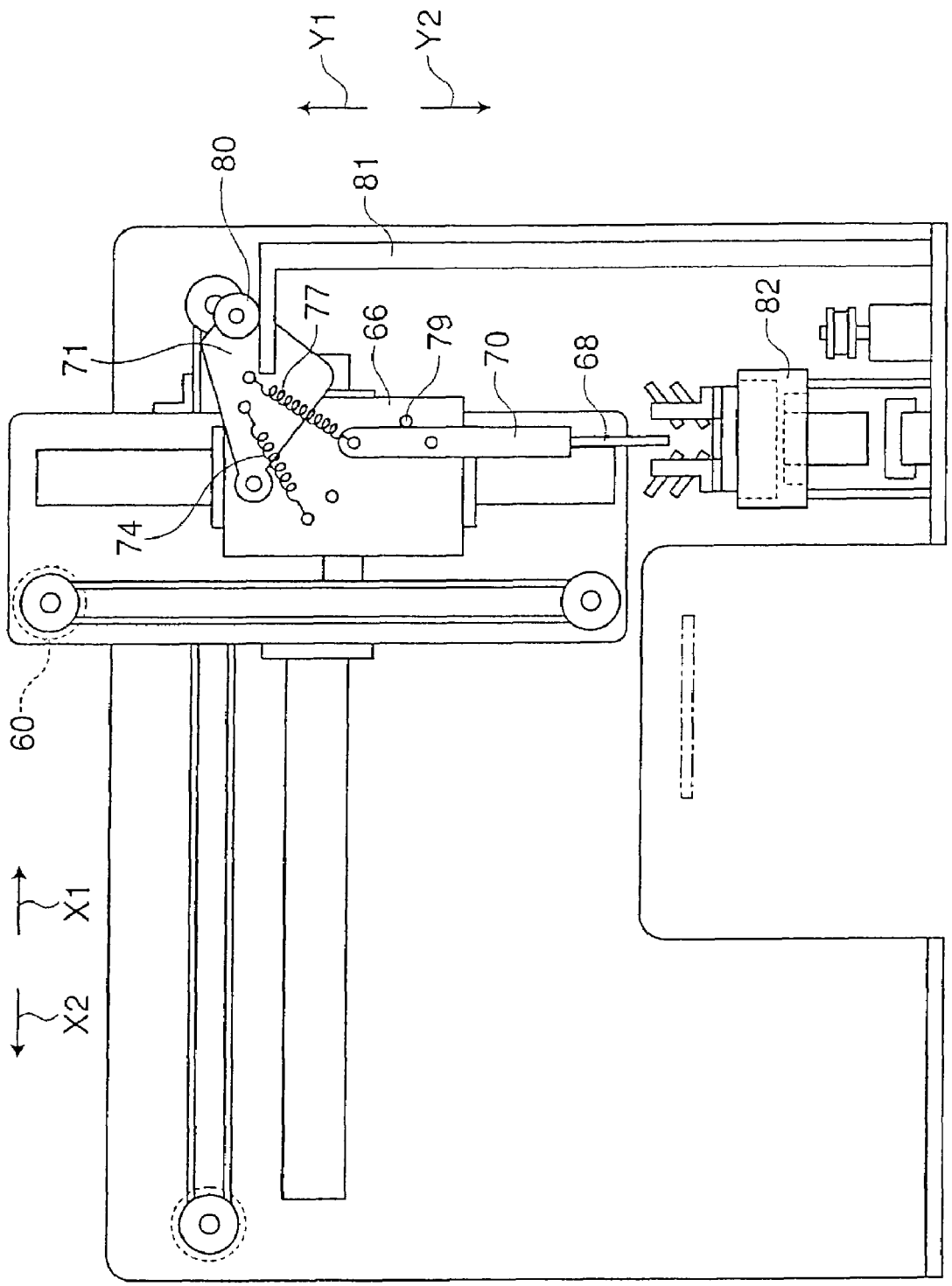
FIG. 9 is a view illustrating the operation of the smearing mechanism according to the present invention.

Subsequently, the stepping motor 60 is driven to move the vertically moving plate 66 in the direction of the arrow Y2. Then, the cam 71 rotates in a counterclockwise direction since the bearing 80 is engaged with the bracket 81. Therefore, the end of the support arm 70 is pulled by the spring 77, rotated in a clockwise direction and latched by the stop pin 79 to be maintained in a vertical state, as shown in FIG. 9.

Figure 10:
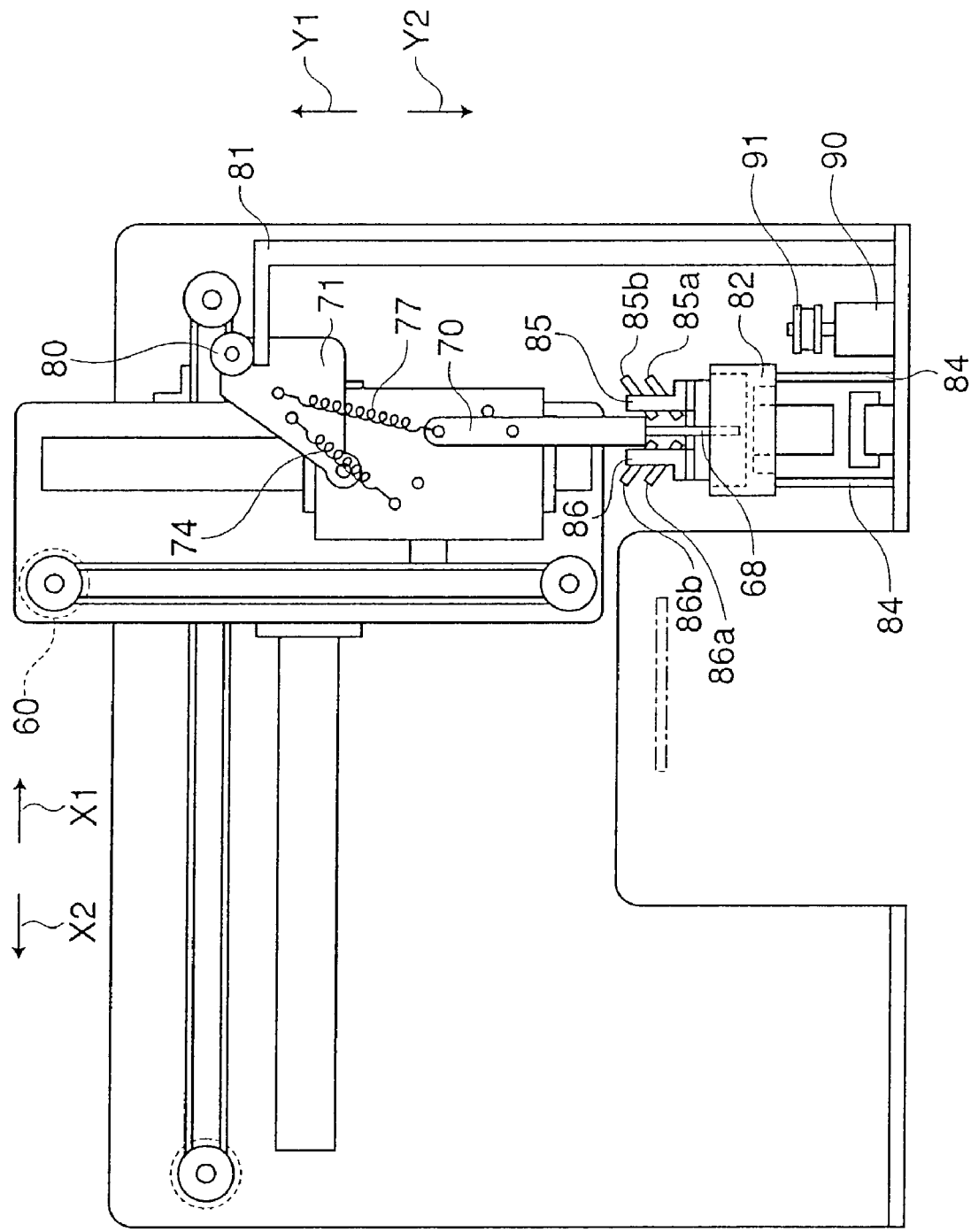
FIG. 10 is a view illustrating the operation of the smearing mechanism according to the present invention.

Further, the stepping motor 60 is driven to allow the vertically moving plate 66 to descend in the direction of the arrow Y2, thereby the edge of the spreader glass 68 is introduced in a washing bath 82 as shown in FIG. 10.

Figure 11:
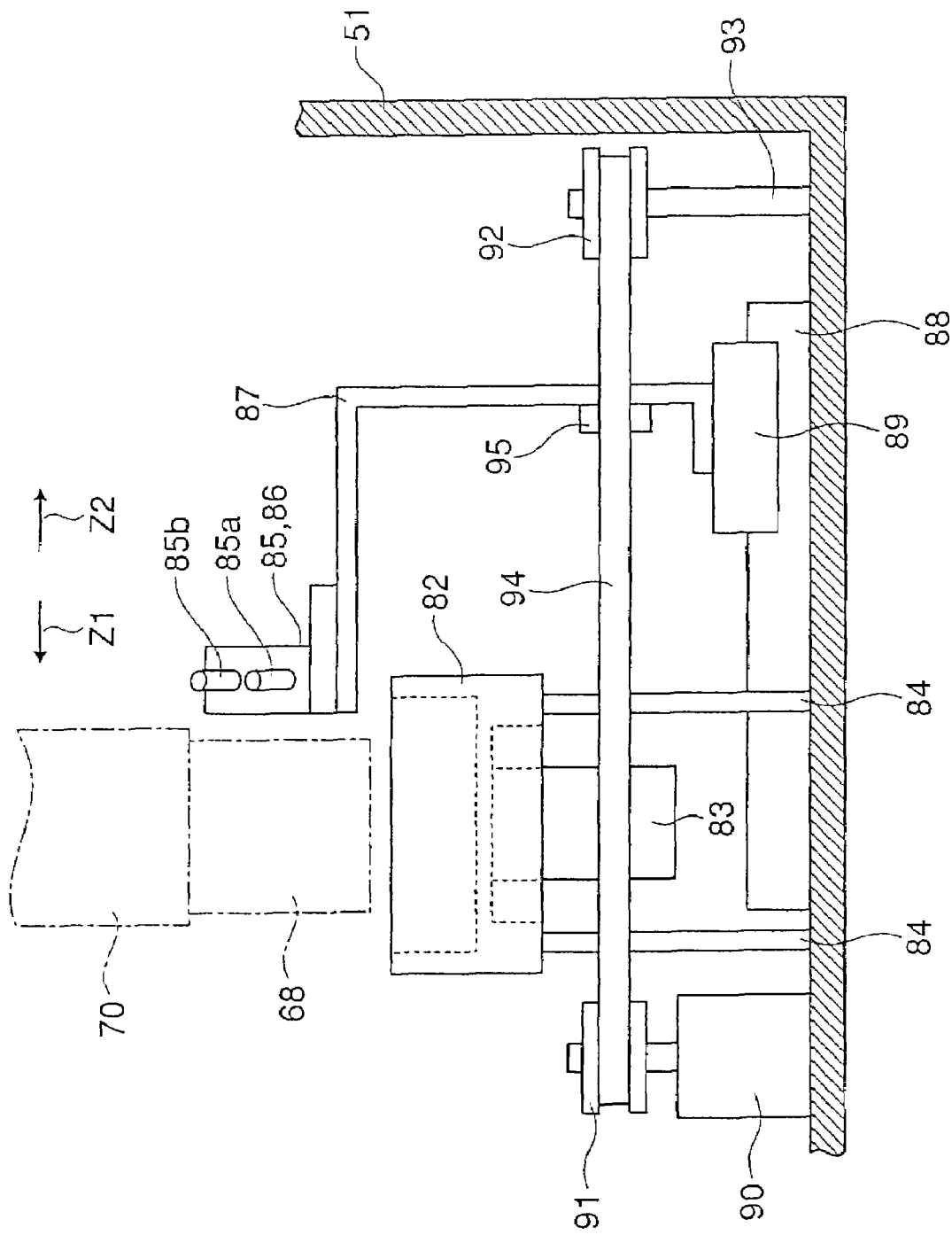
FIG. 11 is a fragmentary view taken in the direction of arrows along a line A-A of FIG. 6.

FIG. 11 is a fragmentary view taken in the direction of arrows along a line A-A of FIG. 6, illustrating the mechanism of the washing section for washing the spreader glass 68.

Figure 12:
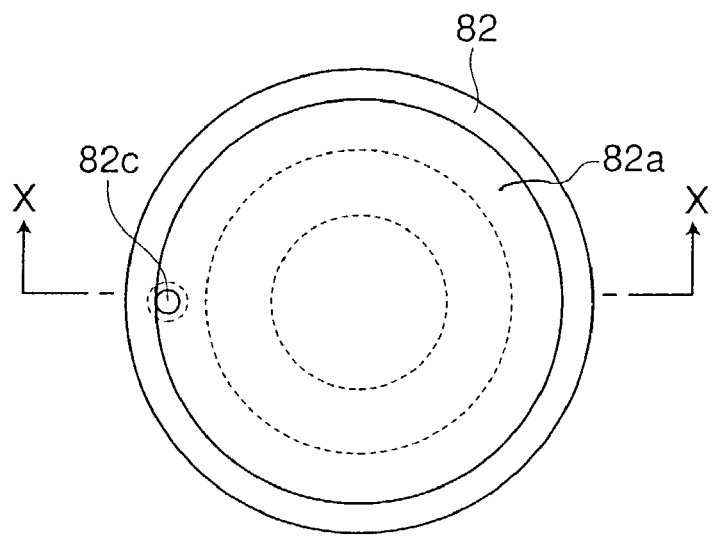
FIG. 12 is a top view illustrating a washing bath according to the present invention.
Figure 13:
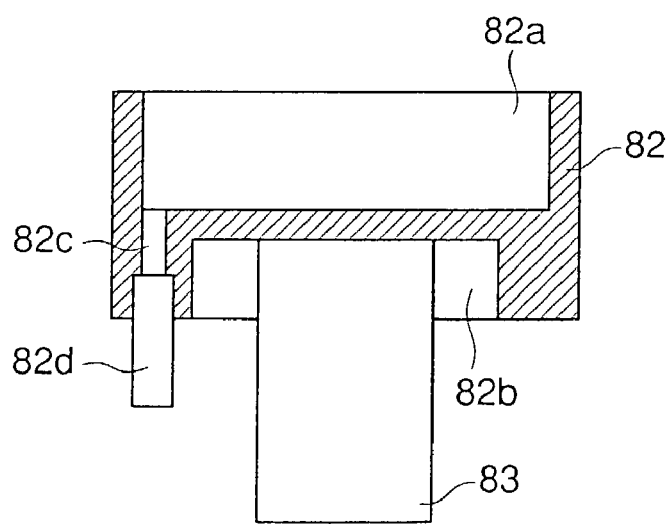
FIG. 13 is a fragmentary view taken in the direction of arrows along a line X-X of FIG. 12.

FIG. 12 is a top view of a washing bath 82 and FIG. 13 is a fragmentary view taken in the direction of arrows along a line X-X of FIG. 12. As shown in FIGS. 12 and 13, the washing bath 82 made of stainless steel is in the form of a cylinder and provided with a cylindrical concave portion 82a at the top for storing washing liquid and a concave portion 82b at the bottom for installing a transducer therein. On the bottom of the concave portion 82b, a drain outlet 82c is opened in which a nipple 82d is provided. A cylindrical ultrasonic transducer 83 is installed in the concave portion 82b.

As shown in FIGS. 10 and 11, the washing bath 82 is supported on four columns 84. A pair of nozzle heads 85 and 86 facing to each other is mounted on a bracket 87. The nozzle heads 85 and 86 are equipped with washing liquid discharge nozzles 85a and 86a and drying air discharge nozzles 85b and 86b, respectively. The washing liquid discharge nozzles 85a and 86a are facing to each other and so are the drying air discharge nozzles 85b and 86b.

The bracket 87 is mounted on a sliding member 89 which is slidably supported on a rail 88 placed on the base plane 51. A stepping motor 90 is mounted on the base plane 51 and a drive pulley 91 is fixed to an output shaft of the stepping motor 90. A follower pulley 92 corresponding to the drive pulley 91 is freely rotatably mounted on the base plane 51 via a shaft 93. A timing belt 94 is entrained about the pulleys 91 and 92 and the bracket 87 is connected to the timing belt 94 via a connecter 95.

When the spreader glass 68 is moved downward in the vertical direction to a position shown in FIG. 11 as mentioned above, the stepping motor 60 is stopped and the spreader glass 68 is maintained in the position.

Then, the stepping motor 90 is driven to move the nozzle heads 85 and 86 in the direction of an arrow Z1 and the washing liquid (physiologic saline) is discharged from the nozzles 85a and 86a toward the spreader glass 68. After the nozzle heads 85 and 86 have passed over the spreader glass 68 from end to end, the stepping motor 90 is stopped to stop the nozzle heads 85 and 86.

At the same time, the discharge of the washing liquid from the nozzles 85a and 86a is also stopped. Thereby, the edge of the spreader glass 68 is washed and uniformly wetted with the washing liquid. The washing liquid discharged from the nozzles 85a and 86a is stored in the concave portion 82a of the washing bath 82.

Then, the stepping motor 60 is driven to move the spreader glass 68 downward in the vertical direction to a position shown in FIG. 10 so that the edge of the spreader glass 68 is sufficiently immersed in the washing liquid in the concave portion 82a. At the same time, the ultrasonic transducer 83 is driven.

Figure 16:
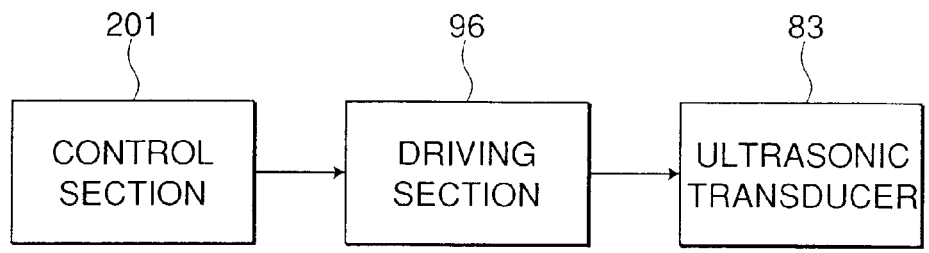
FIG. 16 is a block diagram illustrating a driving circuit of an ultrasonic transducer according to the present invention.
Figure 17A:
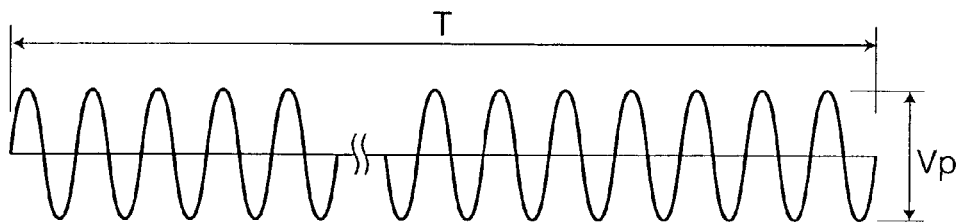
FIGS. 17(a) to 17(c) are diagrams illustrating driving voltage waveforms of the ultrasonic transducer according to the present invention.
Figure 17B:
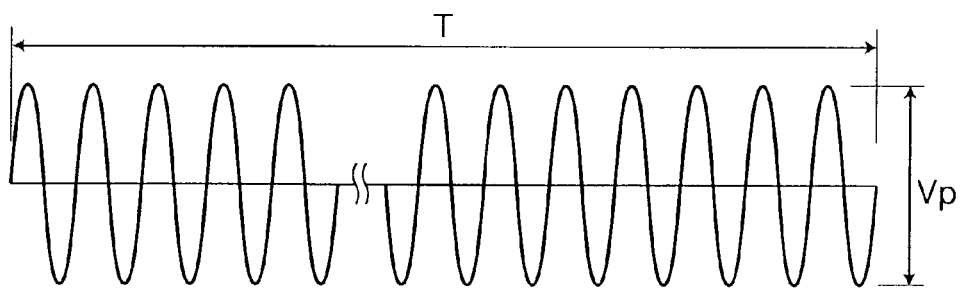
Figure 17C:
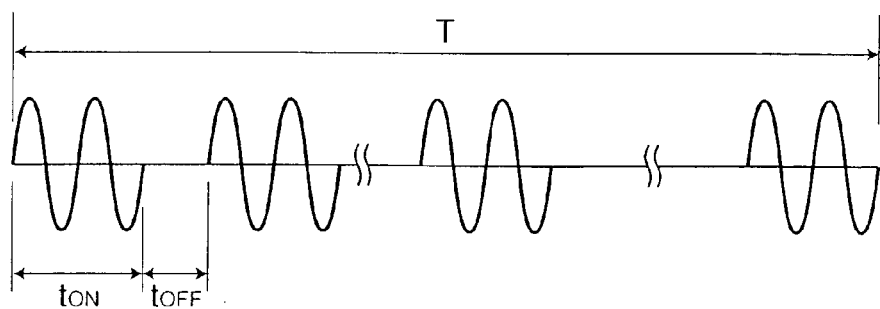

FIG. 16 is a block diagram illustrating a driving circuit of the ultrasonic transducer 83. A driving section 96 is equipped with an inverter which outputs an a.c. voltage of 67 kHz to the ultrasonic transducer 83. The control section 201 controls amplitude Vp of the output voltage of the driving section 96 as shown in FIGS. 17(a) or 17(b), or alternatively, intermits the output periodically as shown in FIG. 17(c) to control an ON period $t_{ON}$ and an OFF period $t_{OFF}$, thereby adjusting the oscillation energy applied by the ultrasonic transducer 83 to the washing liquid via the washing bath 82.

The control section 201 calculates the viscosity of the sample which is smeared on the slide glass 10 by using the spreader glass 68 in the above-described smearing process based on at least one of the number of erythrocytes, the number of leukocytes, the amount of hemoglobin and the hematocrit value that have been obtained from the sample (the higher these values are, the higher the viscosity of the sample is). The control section 201 adjusts the amplitude Vp of the output voltage or the ON-OFF period of the driving section 96 based on the calculated viscosity. Then, in accordance with the adjusted output voltage, the ultrasonic transducer 83 is driven for time T (e.g., 10 seconds). That is, the driving section 96 drives the ultrasonic transducer 83 to increase the ultrasound responsive to an increase in the calculated viscosity.

Thus, the ultrasonic transducer 83 applies optimum oscillation energy to the washing liquid in the concave portion 82a to effectively wash away the remaining sample adhered to the spreader glass 68. When the time T has passed and the transducer 83 is stopped, the stepping motor 60 is driven to pull the spreader glass 68 out of the washing liquid and move it upward to a position shown in FIG. 11. At the same time, the washing liquid is drained away through the drain outlet 82c.

Subsequently, drying air is discharged from the drying air discharge nozzles 85b and 86b. At the same time, the stepping motor 90 is driven to shift the nozzle heads 85 and 86 toward the direction of an arrow Z2 to a position shown in FIG. 11. When the nozzle heads 85 and 86 are returned to the position shown in FIG. 11, the nozzles 85b and 86b stop the discharge of the drying air. Thus, the spreader glass 68 is dried.

Then, the stepping motors 52 and 60 are driven to move the horizontally moving plate 58 and the vertically moving plate 66, thereby returning the spreader glass 68 to an initial position shown in FIG. 6. Thus, the spreader glass 68 is ready for the next smearing.

Figure 14:
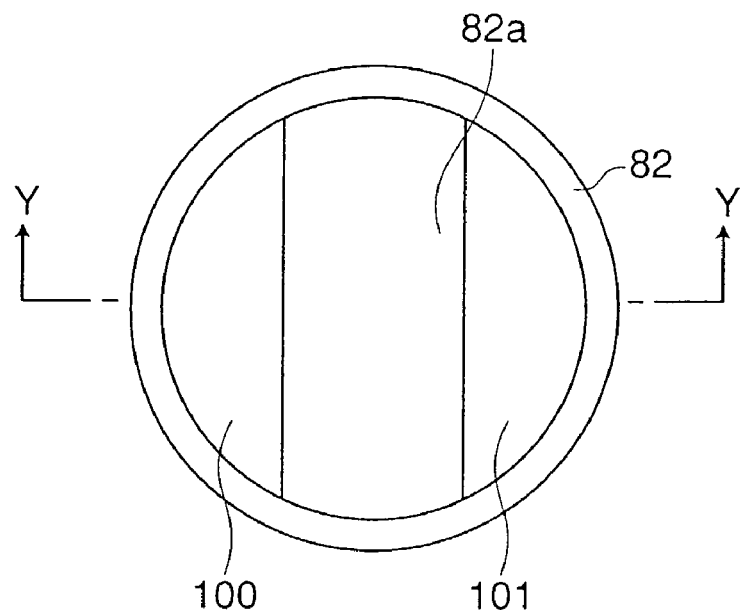
FIG. 14 is a top view illustrating a variant example of the washing bath according to the present invention.
Figure 15:
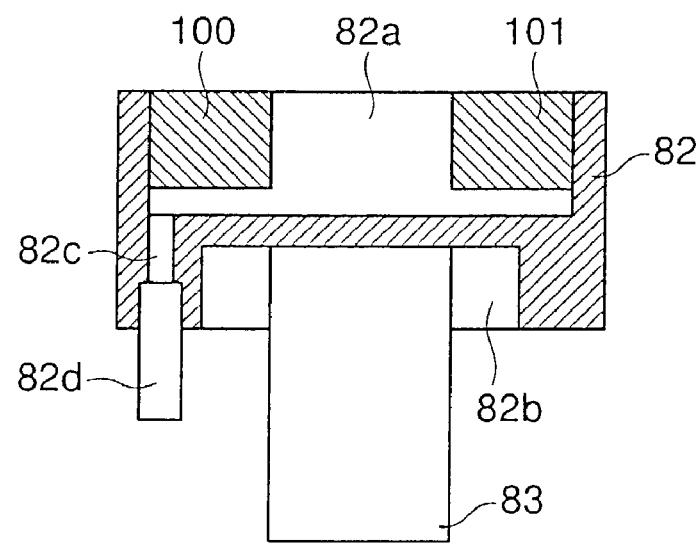
FIG. 15 is a fragmentary view taken in the direction of arrows along a line Y-Y of FIG. 14.

FIG. 14 is a view corresponding to FIG. 12 illustrating a modified example of the washing bath and FIG. 15 is a fragmentary view taken in the direction of arrows along a line Y-Y of FIG. 14. The modified washing bath is made by adhering two semi-cylinder parts 100 and 101 made of a resin to the inner wall of the cylindrical concave portion 82a of the washing bath 82. By providing the semi-cylinder parts 100 and 101, the volume of the concave portion 82 is reduced, which saves the amount of the washing liquid required for washing.

According to the present invention, the ultrasound is applied to the washing section and the spreader glass is effectively washed under ultrasound.

What is claimed is:

1. An automatic smear preparing apparatus comprising:
    a sample smearing section comprising a first supplier configured for supplying a slide glass to a predetermined position, a second supplier configured for supplying a biological sample on the supplied slide glass, and a spreader glass configured for spreading the biological sample on the slide glass;
    a washing section for washing the spreader glass, the washing section comprising a washing bath to immerse the spreader glass in a washing liquid;
    a transferring section configured for transferring the spreader glass to the washing section;
    an ultrasonic generating section configured for supplying ultrasound to the washing bath;
    a drying section comprising nozzle means for discharging a drying air to both sides of the washed spreader glass; and
    a shifting section configured for shifting the nozzle means when the nozzle means discharges the drying air to the washed spreader glass.

2. The automatic smear preparation apparatus according to claim 1 wherein the ultrasonic generating section includes an ultrasonic transducer and a driving section for driving the ultrasonic transducer, the driving section being adapted to drive the ultrasonic transducer to control the ultrasound responsive to a viscosity of the biological sample.

3. The automatic smear preparing apparatus according to claim 2, wherein the driving section adjusts the ultrasound by changing amplitude of the ultrasound.

4. The automatic smear preparing apparatus according to claim 2, wherein the driving section intermittently drives the ultrasound transducer in a predetermined period to adjust the ultrasound.

5. The automatic smear preparing apparatus according to claim 1, wherein the transferring section puts the spreader glass in and out of the washing bath.

6. The automatic smear preparing apparatus according to claim 1, wherein the washing bath contains a water or a physiologic saline as the washing liquid.

7. The automatic smear preparing apparatus according to claim 1, wherein the ultrasonic generating section includes an ultrasonic transducer arranged in the washing bath.

8. The automatic smear preparing apparatus according to claim 5, wherein the ultrasonic generating section includes an ultrasonic transducer and a driving section for driving the ultrasonic transducer, the driving section driving the ultrasonic transducer when the spreader glass is taken out of the washing bath.

9. The automatic smear preparing apparatus according to claim 7, wherein the ultrasonic transducer has a frequency range of 50 to 80 kHz.

10. An automatic smear preparing apparatus comprising:
a sample smearing section including a spreader glass for smearing a biological sample on a slide glass;
a washing section for washing the used spreader glass;
an ultrasonic generating section applying ultrasound to the washing section; and
a nozzle for discharging drying air onto the washed spreader glass,
wherein the washing section includes a sub-washing section spraying washing liquid onto the spreader glass and a main washing section which immerses the spreader glass in the washing liquid.

11. An automatic blood smear preparing apparatus comprising:
a sample smearing section comprising a first supplier configured for supplying a slide glass to a predetermined position, a second supplier configured for supplying a blood sample on the supplied slide glass, and a spreader glass configured for spreading the blood sample on the slide glass;
a washing section for washing the spreader glass to remove the blood sample, the washing section comprising a washing bath to immerse the spreader glass in a washing liquid;
a transferring section configured for transferring the spreader glass to the washing section;
an ultrasonic generating section configured for supplying ultrasound to the washing bath; and
a drying section comprising nozzle means for discharging a drying air to both sides of the washed spreader glass.

12. The automatic blood smear preparing apparatus according to claim 11 further comprising:
a shifting section configured for shifting the nozzle means when the nozzle means discharges the drying air to the washed spreader glass.

* * * * *